(12) United States Patent
Weilhoefer et al.

(10) Patent No.: US 8,671,996 B2
(45) Date of Patent: Mar. 18, 2014

(54) METHOD AND DEVICE FOR FILLING AND/OR EMPTYING A DIALYSIS MACHINE

(75) Inventors: Thomas Weilhoefer, Niederwerrn (DE); Georg Zehner, Uechtelhausen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1142 days.

(21) Appl. No.: 12/449,775

(22) PCT Filed: Feb. 26, 2008

(86) PCT No.: PCT/EP2008/001515
§ 371 (c)(1),
(2), (4) Date: Aug. 26, 2009

(87) PCT Pub. No.: WO2008/104367
PCT Pub. Date: Sep. 4, 2008

(65) Prior Publication Data
US 2010/0078092 A1    Apr. 1, 2010

(30) Foreign Application Priority Data
Feb. 26, 2007 (DE) .................. 10 2007 009 269

(51) Int. Cl.
*B01D 61/26* (2006.01)
(52) U.S. Cl.
USPC .......... 141/65; 141/1; 141/9; 141/82; 141/231
(58) Field of Classification Search
USPC ............... 141/1, 2, 9, 18, 65, 82, 231
See application file for complete search history.

(56) References Cited

U.S. PATENT DOCUMENTS

| | | | |
|---|---|---|---|
| 3,690,340 A | | 9/1972 | Sipin |
| 4,386,634 A | * | 6/1983 | Stasz et al. .................... 141/2 |
| 5,645,734 A | * | 7/1997 | Kenley et al. ................ 210/805 |
| 5,651,893 A | * | 7/1997 | Kenley et al. ................ 210/636 |
| 5,674,390 A | * | 10/1997 | Matthews et al. ............ 210/261 |
| 5,762,782 A | * | 6/1998 | Kenley et al. .................. 210/85 |
| 5,788,099 A | | 8/1998 | Treu et al. |
| 5,951,859 A | * | 9/1999 | Miura et al. .................. 210/192 |
| 6,758,975 B2 | * | 7/2004 | Peabody et al. ............. 210/645 |
| 6,787,032 B2 | * | 9/2004 | Kurome et al. ............ 210/257.1 |

(Continued)

FOREIGN PATENT DOCUMENTS

| | | |
|---|---|---|
| CN | 1388761 | 1/2003 |
| CN | 1602210 | 3/2005 |

(Continued)

*Primary Examiner* — Gregory Huson
*Assistant Examiner* — Nicolas A Arnett
(74) *Attorney, Agent, or Firm* — Jacobson Holman PLLC (57) ABSTRACT

An apparatus for the filling of a dialyzer with a dialysis liquid and/or for the draining of dialysis liquid from a dialyzer is mobile. The apparatus has at least one liquid container for the reception of a liquid, preferably of RO water, at least one concentrate receptacle for the reception of concentrate and/or a concentrate connection for the connection of a container holding concentrate as well as at least one preparation unit which is arranged and configured such that liquid from the liquid container can be mixed with concentrate from the concentrate receptacle and/or from the container holding the concentrate in the preparation unit.

29 Claims, 3 Drawing Sheets

(56) References Cited

U.S. PATENT DOCUMENTS

| | | | |
|---|---|---|---|
| 6,884,441 B2* | 4/2005 | Pippert et al. | 424/678 |
| 6,945,257 B2* | 9/2005 | Tabani et al. | 134/22.1 |
| 7,077,956 B2* | 7/2006 | Rovatti | 210/258 |
| 7,367,346 B2* | 5/2008 | Tabani et al. | 134/102.1 |
| 2001/0040127 A1* | 11/2001 | Donig et al. | 210/321.71 |
| 2002/0088752 A1 | 7/2002 | Balschat et al. | |
| 2002/0112743 A1* | 8/2002 | Tabani et al. | 134/22.12 |
| 2002/0134721 A1 | 9/2002 | Kurome et al. | |
| 2003/0010703 A1* | 1/2003 | Pippert et al. | 210/321.71 |
| 2004/0069718 A1* | 4/2004 | Sun et al. | 210/748 |
| 2004/0232061 A1* | 11/2004 | Dillon | 210/257.2 |
| 2008/0125693 A1* | 5/2008 | Gavin et al. | 604/29 |

FOREIGN PATENT DOCUMENTS

| | | |
|---|---|---|
| DE | 196 05 260 A1 | 11/1996 |
| JP | H05-176991 | 7/1993 |
| JP | H05-063549 | 8/1993 |
| JP | H09-000618 | 1/1997 |
| JP | H09-122229 | 5/1997 |
| JP | H11-508469 | 7/1999 |
| JP | 2000-005303 | 1/2000 |
| JP | 2001-293083 | 10/2001 |
| JP | 2005 279136 | 10/2005 |
| WO | WO 96/25214 | 8/1996 |
| WO | WO 97/02056 | 1/1997 |
| WO | WO 00/53291 | 9/2000 |

* cited by examiner

METHOD AND DEVICE FOR FILLING AND/OR EMPTYING A DIALYSIS MACHINE

CROSS-REFERENCE TO RELATED APPLICATIONS

This is a national stage of PCT/EP08/001,515 filed Feb. 26, 2008 and published in German, which has a priority of German no. 10 2007 009 269.7 filed Feb. 26, 2007, hereby incorporated by reference.

BACKGROUND OF THE INVENTION

1. Field of Invention

The present invention relates to an apparatus and to a method for the filling of a dialyzer with a dialysis liquid and/or for the draining of a dialysis liquid from a dialyzer. The invention further relates to the use of an apparatus for the filling of a dialyzer with a dialysis liquid and/or for the draining of a dialysis liquid from a dialyzer.

2. Description of the Prior Art

Hemodialyzers are known from the prior art in which the dialysis liquid is not prepared during a treatment, but in which rather the total amount of dialysis liquid required for a dialysis treatment is provided in a tank of the dialyzer prior to the treatment. Dialyzers of this type are also called "batch-type" dialyzers. With a suitable arrangement of the inflow and of the outflow of the tank, it can be used not only for the stocking of the ready-to-use dialysis liquid, but also for the reception of consumed dialysis liquid. More detailed explanations on batch-type dialyzers can be found in the article "Batch-type dialysis machines" in "Replacement of Renal Function by Dialysis", 5th Edition, Kluwer Academic Publishers, 2004, 369-371, to which reference is herewith made.

In units of this type of the applicant, two additional units are used for the preparation of the dialysis liquid, one of said units being a water tank for RO water (RO=reverse osmosis) and the other being a unit for the manufacture of the dialysis liquid. In this connection, the two units are in communication with one another such that water is conducted out of the water tank by means of a pump through a chamber of the unit for the manufacture of the dialysis liquid in which the concentrates designed for the treatment are located in solid and/or liquid form. A specific amount of RO water is flushed through this chamber without a fixed mixing ratio being significant during the inflow procedure. The amounts of the concentrate or concentrates and of the water fine-tuned for a treatment mix sufficiently to obtain a homogeneous dialysis liquid in the tank of the dialyzer.

The two named units, that is the RO water tank, on the one hand, and the unit for the manufacture of the dialysis liquid, on the other hand, have a fixed location in a dialysis clinic, i.e. they are arranged in a stationary location. The individual dialyzers are moved to this location so that they can be filled with the dialysis liquid prior to a treatment. The dialyzers filled with dialysis liquid in this manner are then moved to the location of the dialysis treatment. Subsequently to the dialysis treatment, the dialyzers are emptied at the said fixed location and cleaned and disinfected.

A system of this type for the filling and emptying of dialyzers is associated with a comparatively high installation effort so that its procurement cannot be worthwhile for small dialysis centers. Apart from this, the known system has proved to be inflexible to the extent that the units required for the manufacture of the dialysis liquid are arranged at a stationary location.

SUMMARY OF THE INVENTION

It is therefore the object of the present invention to further develop an apparatus and a method of the first named type such that they can be provided and carried out respectively with a comparatively low effort and can moreover be used more flexibly with respect to the previously known system.

This object is solved by an apparatus and a method having the features described herein.

Provision is made, as described herein, for the apparatus for the filling of a dialyzer with a dialysis liquid and/or for the draining of dialysis liquid from a dialyzer to be mobile and to have at least one liquid container for the reception of a liquid, preferably of RO water, at least one concentrate receptacle for the reception of concentrate and/or a concentrate connection for the connection of a container holding concentrate as well as at least one preparation unit which is arranged and configured such that liquid from the liquid container can be mixed with concentrate from the concentrate receptacle and/or from the container holding the concentrate in the preparation unit.

A mobile unit or a mobile housing is thus provided by the present invention which combines the functions of the aforesaid units for the manufacture of a dialysis liquid known from the prior art. It is possible due to the mobility of the apparatus in accordance with the invention to move it to a dialyzer and fill the dialyzer as required with ready-to-use dialysis liquid by means of the apparatus or to drain consumed dialysis liquid from the dialyzer and to clean and/or disinfect it. The individual dialyzers do not have to be moved for the purpose of filling and/or emptying or cleaning and disinfecting, even though this is also naturally not precluded within the framework of the present invention.

Provision is made in an aspect of the invention for the preparation unit and the concentrate receptacle into which the concentrate is filled to be formed by one and the same component. It is conceivable, for example, that the concentrate is introduced into the concentrate receptacle in solid and/or liquid form and for the concentrate receptacle then to be flushed with liquid, preferably with RO water, whereby the dialysis liquid is manufactured which can then be dispensed to a dialyzer.

It must be pointed out at this point that the term "dialysis liquid" within the framework of the present invention does not necessarily mean that the dialysis liquid is ready to use. The case is also conceivable that certain components of a dialysis liquid are made available by the apparatus in accordance with the invention and by the method in accordance with the invention and that, for example, even further additives are added in the dialyzer itself or that a complete mixing or solution of the components of the dialysis liquid only takes place in the tank of the dialyzer. Provision is, however, made in a preferred aspect of the invention for a dialysis liquid ready for use to be made available by means of the apparatus in accordance with the invention and by means of the method in accordance with the invention which is supplied to the dialyzer and can then be used for the dialysis treatment.

Provision is made in a further aspect of the invention for the preparation unit to be arranged and configured such that it is flushed by liquid from the liquid container in the operation of the apparatus. A mixing of the concentrate or concentrates with the liquid takes place in this context. This mixture is flushed into the tank of a dialyzer and is present there in the form of a homogeneous solution fine-tuned to the patient to be treated.

The apparatus can have a first connector for the purpose of the dispensing of the dialysis liquid into a dialyzer which is in communication with or can be connected to the preparation unit. This first connector can be configured, for example, in the form of an adapter which permits a reliable connection to a dialyzer.

Furthermore, the apparatus can have a second connector for the purpose of emptying a dialyzer for the reception or drainage of consumed dialysis liquid from a dialyzer. It is possible to first receive the consumed dialysis liquid from the dialyzer in the apparatus in accordance with the invention in order to drain it from the apparatus at a later time. It is likewise conceivable to conduct the consumer dialysis liquid via the apparatus in accordance with the invention to a drain with which the apparatus is in communication.

Provision can furthermore be made for the apparatus to have a third connection for the supply of a gas or of a cleaning liquid to a dialyzer for the purpose of emptying and/or cleaning the dialyzer. The gas can, for example, be air to which a disinfectant has been added for the disinfection of the dialyzer to be emptied or already emptied. The cleaning liquid can be RO water, for example. The cleaning liquid can naturally also contain a suitable disinfectant.

It is conceivable that the second connector, by means of which consumed dialysis liquid is removed from the dialyzer, and the third connector, by means of which the gas, for example air enriched with disinfectant or a cleaning liquid, is supplied to the dialyzer, to be arranged in a common adapter which permits a reliable connection to the dialyzer.

In a further aspect of the invention, the apparatus has a conveying device which is arranged and configured such that liquid can be conveyed out of the liquid container into the preparation unit by means of the conveying device and/or that a mixture of liquid and concentrate can be conveyed out of the preparation unit to a dialyzer by means of the conveying device.

It is furthermore conceivable that the apparatus has a conveying device which is arranged and configured such that gas or liquid, for example air or liquid enriched with a disinfectant or a flushing solution, can be conveyed to the third connector of the apparatus by means of the conveying device.

It is conceivable that the two named conveying devices are formed by one and the same component. It is, for example, conceivable that the conveying device is formed by a pump or by a compressor.

Provision is made in a further aspect of the invention for a container to be arranged in the line between the conveying device and the third connector for the reception of disinfectant, with the container being arranged such that it dispenses disinfectant to the gas or liquid flowing through the line.

The apparatus can have a unit for the manufacture of RO water. The RO water manufactured therein is supplied to the liquid container and is stored there until it is required for the manufacture of the dialysis liquid.

It is also conceivable that the apparatus has a fourth connector via which a liquid, in particular RO water, can be supplied to the liquid container.

The apparatus in accordance with the invention can thus have a separate unit for the manufacture of RO water; however, this is not absolutely necessary. If such a unit is not provided, the apparatus can be provided with a connector via which the apparatus or the liquid container can be supplied with RO water from a supply line or from an external RO unit.

In a further aspect of the invention, a heating device is provided by means of which the liquid contained in the liquid container and/or the liquid supplied to the liquid container and/or the liquid flowing out of the liquid container can be heated.

It is also conceivable to arrange a heating device H such that the preparation unit and/or the mixture flowing out of the preparation unit can be heated by it.

The present invention further relates to a method for the filling of a dialyzer with a dialysis liquid and/or for the draining of dialysis liquid from a dialyzer which is characterized by the fact that, for the purpose of filling the dialyzer, in a first step, the dialysis liquid is manufactured in a mobile apparatus and that, in a second step, the dialysis liquid is dispensed to a dialyzer by the mobile apparatus, and/or in that dialysis liquid is removed from the dialyzer by means of a mobile apparatus for the purpose of emptying a dialyzer.

Provision can be made in this connection for the dialysis liquid to be manufactured in the apparatus from at least one liquid, preferably from RO water, and from at least one concentrate, with both the liquid and the concentrate being stored in the apparatus.

It is furthermore conceivable for the concentrate to be supplied to a preparation unit or to be presented in it and for the preparation unit then to be flushed with a liquid, preferably with RO water, for the manufacture of the dialysis liquid.

Provision is made in a further aspect of the invention for compressed air to be generated by means of a compressor and for the compressed air to convey liquid from a liquid container into a preparation unit in which the liquid is mixed with concentrate.

Provision can furthermore be made for compressed air to be generated by means of a compressor and for the compressed air to be supplied to a dialyzer in which it displaces consumed dialysis liquid from the dialyzer to be emptied.

It is conceivable for the compressor in accordance with claim 20 and the compressor in accordance with claim 21 to be formed by the same component and for compressed air to be conveyed by the compressor into the liquid container in a first operating mode in which a dialyzer is filled with dialysis liquid and for compressed air to be conducted by the compressor to the dialyzer in a second operating mode in which a dialyzer is emptied of dialysis liquid.

Provision is made in a further aspect of the invention for compressed air to be generated by means of a compressor and for the compressed air to convey liquid from a liquid container into the dialyzer for the purpose of flushing a dialyzer.

Provision is made in a further aspect of the invention for compressed air first to be supplied to the dialyzer in the second operating mode for the purpose of emptying the dialyzer, with dialysis liquid being displaced from the dialyzer by said compressed air and for subsequently compressed air to be supplied to a liquid container for the purpose of flushing the dialyzer, by means of which compressed air liquid is supplied to the dialyzer.

Provision can be made in a further aspect of the invention for a disinfectant to be supplied to the compressed air before the supply to the dialyzer. Alternatively or additionally, it is likewise possible for the liquid serving the flushing to be provided with a disinfectant.

The apparatus used within the framework of the method in accordance with the invention can be an apparatus as described herein.

The invention furthermore relates to the use of an apparatus as described herein for the filling of a dialyzer with a dialysis liquid and/or for the draining of dialysis liquid from a dialyzer.

BRIEF DESCRIPTION OF THE DRAWINGS

Further details and advantages of the invention will be explained in more detail with reference to an embodiment shown in the drawing. There are shown.

DETAILED DESCRIPTION OF THE PREFERRED EMBODIMENTS

Figure 1:
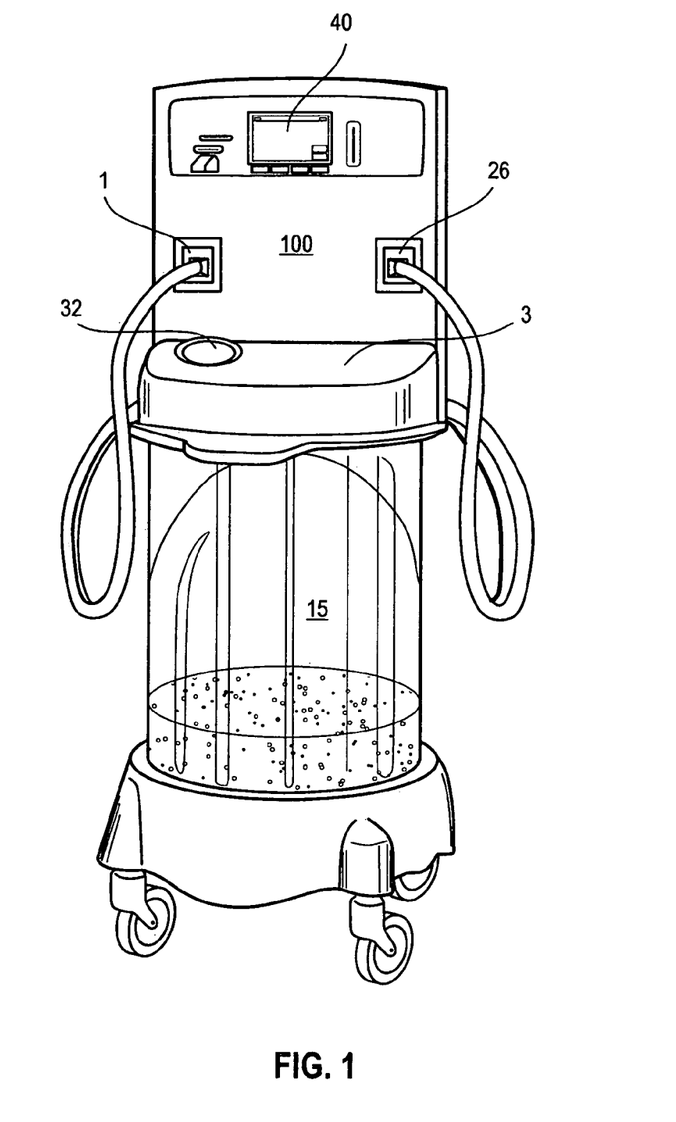
FIG. 1: the apparatus in accordance with the invention in a front view.
Figure 3:
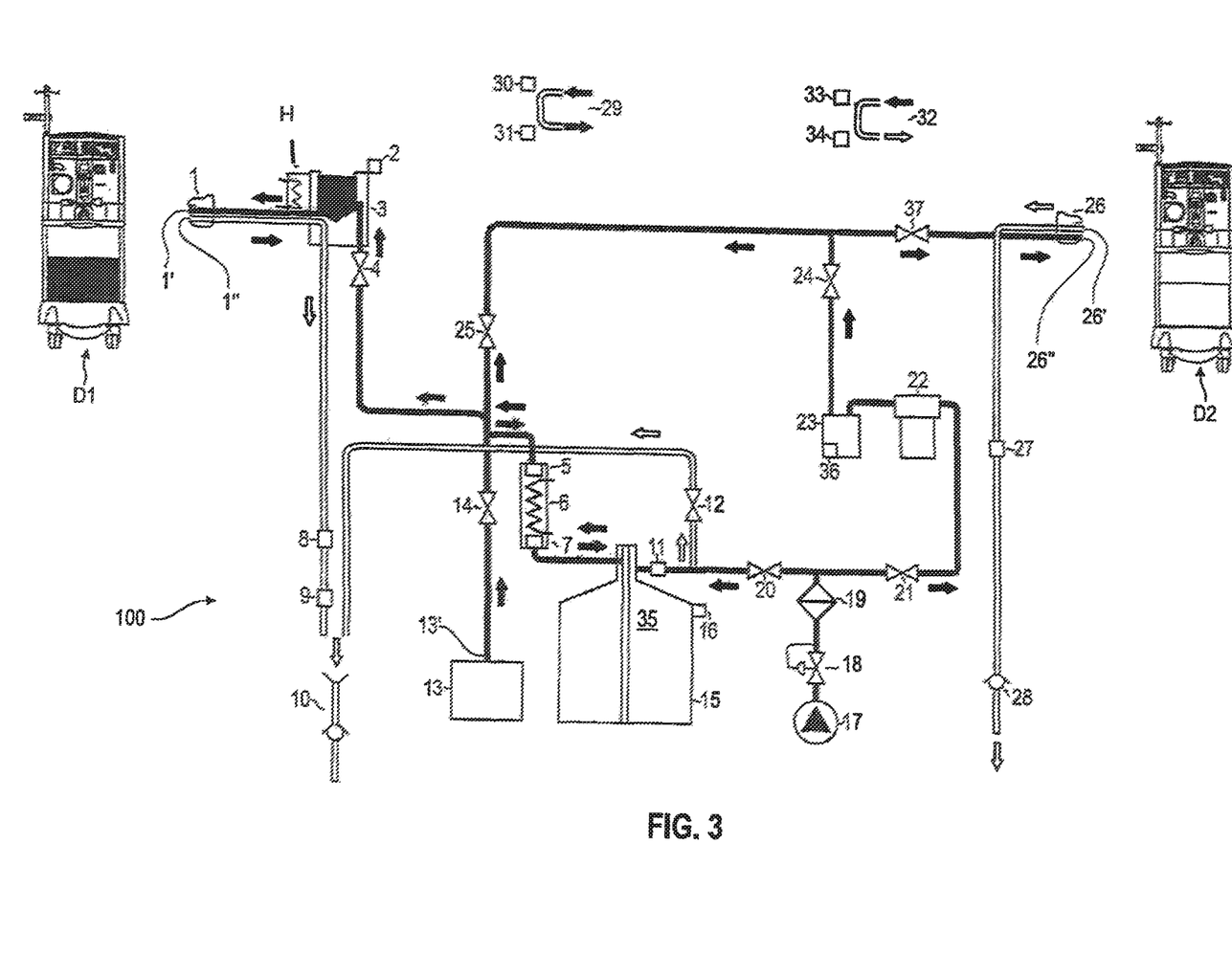
FIG. 3: a schematic representation of the components as well as of the lines of the apparatus in accordance with the invention connecting them.

FIG. 1 shows the apparatus 100 in accordance with the invention which serves the filling and the emptying of batch-type dialyzers D1 and D2 which are shown in FIG. 3 at the left and at the right of the apparatus 100.

The apparatus 100 has a liquid container 15, and a concentrate receptacle 3 which serves the reception of the concentrate or concentrates and further more as a preparation unit for the preparation for the dialysis liquid. The unit shown in FIG. 1 requires a power connection, a waste water connector and an RO unit 13 which is shown to the left of the apparatus 100 in accordance with the invention in FIG. 2. As already stated above, it is likewise conceivable and covered by the invention not to use an external RO unit, but rather to arrange an RO unit in the apparatus 100 in accordance with the invention itself.

The liquid container 15 is formed by a glass tank holding 120 l. The concentrate receptacle (and preparation unit) 3, in which the concentrate is mixed with RO water from the liquid container 15, is located above the glass tank of liquid container 15. The concentrate receptacle and preparation unit 3 has an opening which is closed by a cover 32 and through which the concentrate, which is solid and/or liquid as required, can be filled in. The concentrate receptacle and preparation unit 3 is configured as a flush pot and is integrated into the work surface. The cover 32 of the flush pot comprises a thick plate with a handle. After this has been put on, it is closed by a mechanism.

As can further be seen from or is indicated in FIG. 1, the required operating elements for the user are arranged in the front part of the apparatus 100. On the one hand, a touch-screen display 40, a bay or a card reader for the unit card of the dialyzer and the receivers for the adapters 1, 26 for the filling and emptying as well as a label printer output are arranged there.

It can be advantageous for customer service work if the front part can be opened.

The hydraulics shown in more detail in FIG. 3 as well as all the required modules are accommodated below the work surface and in the rear region of the unit.

Figure 2:
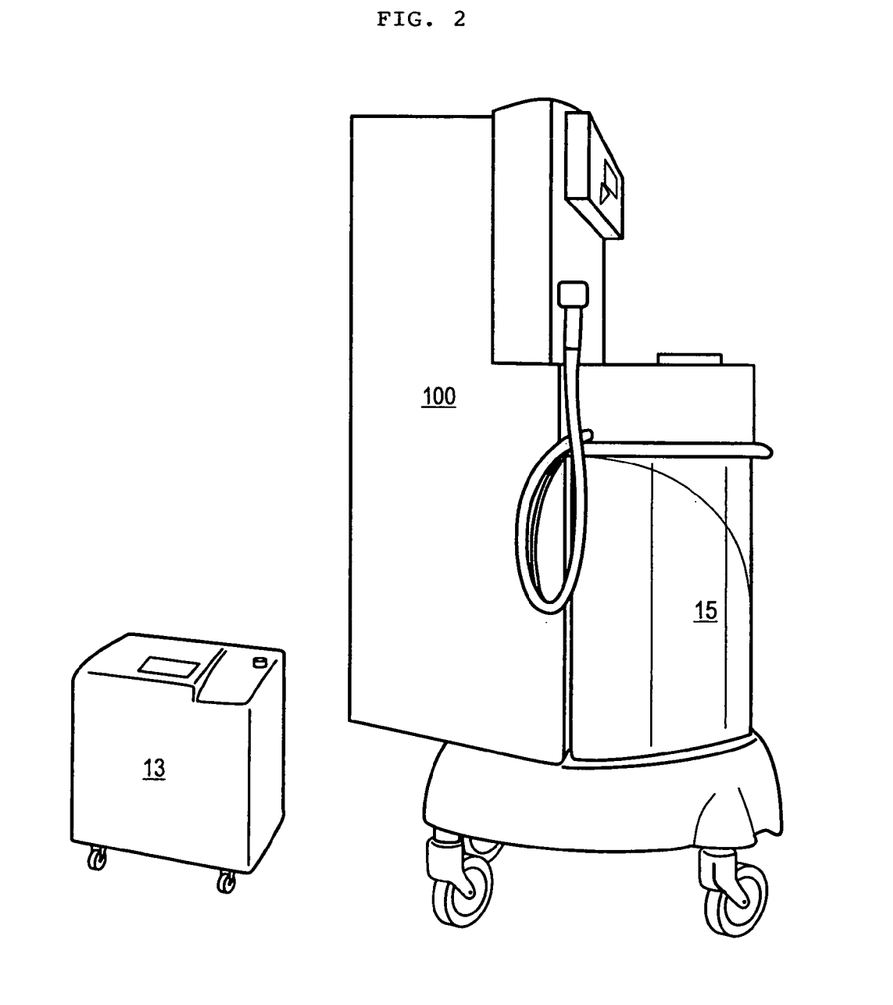
FIG. 2: the apparatus in accordance with the invention in a side view with an external RO unit.

As already stated above, FIG. 2 shows the apparatus in accordance with the invention in a side view as well as an external RO unit 13 as an example for the permeate supply. RO water is manufactured by means of this RO unit 13 and is then received in the liquid container 15 configured as a glass tank and stored in this until the apparatus is used for the manufacture of a dialysis liquid and for the filling of a dialyzer.

If the adapters 1, 26 are not needed for filling and/or emptying, they are plugged in their parking position, as can be seen from FIG. 1. They can be secured against slipping out there by a clamp. It is conceivable for sensors to be provided which recognize whether the adapters 1, 26 are plugged and secured. It is furthermore conceivable that a suitable UV lamp is arranged by means of which germ growth can also be prevented or at least kept within limits at the adapter surface.

Furthermore, a laser scanner is provided for the scanning of concentrates and is integrated in the housing of the apparatus 100. It is conceivable that the scanning procedure remains activated for so long until the desired concentrates have been recognized. This arrangement of an inbuilt scanner has the advantage that hampering cables are omitted and that the user only has to position the concentrates in the laser beam for scanning.

The process of manufacturing a dialysis liquid, of dispensing the dialysis liquid into the dialyzer D1 and of emptying a dialyzer D2 will now be explained with reference to FIG. 3.

Within the framework of the preparation of the manufacture of a dialysis liquid, first, RO water is conducted, for example from the RO unit 13 shown at the left in FIG. 2, via the connector 13', with an open valve 14 and with closed valves 4, 25, over a continuous-flow water heater 6 and heated to 36° C. and is then filled into the liquid container 15 of the apparatus 100. It is then stored in the glass liquid container 15. This has a capacitive sensor 16 which measures the filling level in the liquid container 15. Furthermore, a UV lamp 35 with a protective tube is provided in the liquid container 15 and ensures that the germ infestation does not take place or only takes place to a lesser extent.

Once the consumption amount of, for example, 120 l has been reached, the preparation process is complete.

The concentrate or concentrates is/are filled into the concentrate receptacle and preparation unit 3, which is the aforesaid flushing pot and which is flowed through by the heated liquid from the liquid container 15 for the manufacture of the dialysis liquid.

The dialyzer D1 is first connected to the apparatus 100 by means of the adapter 1 and is registered with the apparatus 100 by means of the unit card. The unit card is checked and if the status is in order, the scanning process for the scanning of the concentrates is released. The concentrates are, for example, a solid concentrate which can e.g. contain the components NaCl, NaHCO$_3$ and glucose and a liquid concentrate which can e.g. contain the components KCl, CaCl$_2$ and MgCl$_2$. The concentrate or concentrates are added to the flush pot 3. The reference numeral 2 designates a sensor for the flush pot cover.

After the connection of a dialyzer D1 to the apparatus 100 by means of the adapter 1, the compressor 17 is set into operation and compressed air is introduced into the container 15 with an open valve 20 and with closed valves 12 and 21 and liquid is thereby conducted from the container 15 via the continuous-flow water heater 6 and is conducted into the flush pot 3 with open valve 4 and closed valves 14 and 25. The liquid at the set temperature mixes there with the concentrate or concentrates and is supplied to the dialyzer D1 via the adapter 1 or its connector 1'. At the same time, air is drained from the dialyzer D1 via the connector 1" of the adapter 1. A conductivity/temperature measuring cell 8 is located in the line draining the air off as is an optosensor 9 via which any overflow can be detected. The reference numeral 10 represents a funnel with a shut-off valve.

It is possible in accordance with the invention no longer to determine the time in particular of the addition of the liquid concentrate in a time-controlled manner, but rather via the capacitive (i.e., filling level) sensor 16 at the glass liquid container 15. The capacitive (i.e., filling level) sensor 16 can thus serve, on the one hand to fill in a predetermined consumption amount into the liquid container 15 and, on the other hand, to determine the exact filling level for the addition of a concentrate if this is meaningful for the dissolving and distribution of the concentrate.

The conductivity and the temperature of the dialysis liquid is then measured and printed. The unit card is released for the dialysis in dependence on the result, whereupon the dialyzer D1 is available for a dialysis treatment.

If a dialyzer D2 filled with consumed dialysis liquid, such as is shown at the right in FIG. 3, should be emptied by means of the apparatus 100, the apparatus 100 is connected to the dialyzer D2 by means of the adapter 26. Compressed air is then generated by means of the compressor 17 and it is then enriched with disinfectant, e.g. peracetic acid, in the disinfectant container 22 with an open valve 21 and closed valve 20. The air charged with disinfectant then flows over a leak monitor 23 having a sensor 36 and with open valves 24 and 37 and a closed valve 25 via the connector 26" of the adapter 26 into the dialyzer D2. In the dialyzer D2, the compressed air displaces the consumed dialysis liquid located therein. The latter moves via the connector 26' of the adapter 26 as well as via a drain line, which likewise forms a component of the apparatus 100 and in which an optosensor 27 and a check valve are arranged, into the drain 28.

After the emptying of the dialyzer D2, it is flushed with RO water, for which purpose the compressor 17 generates compressed air which is conducted into the liquid container 15 with closed valves 12 and 21 and with an open valve 20. From there, liquid is supplied via the adapter 26 to the dialyzer D2 after flowing through the heater 6 with closed valves 4 and 24 and with open valves 25 and 37 and is removed via the drain 28 after flowing through the dialyzer D2.

Temperature sensors and flow monitors at the input and output respectively of the continuous-flow water heater 6 are shown with the reference numerals 5 and 7.

Reference numeral 12 designates a valve for the venting of the liquid container 15.

The reference numerals 18 and 19 finally mark a relief valve or a particle filter for the cleaning of the compressed air.

The reference numerals 29 and 32 designate short-circuit pieces with two sensors each 30, 31 and 33, 34. The short-circuit pieces 29, 32 are plugged into the connectors 1' and 1" of the adapter 1 as well as into the connectors 26' and 26" of the adapter 26 and are provided so that the adapters 1 and 26 can be plugged into the parking positions which can be seen from FIG. 1. One respective sensor recognizes the plugged-in adapter and one respective sensor recognizes the securing of the adapter (by a clamp). In this position, the total hydraulics of the apparatus 100 can be disinfected with the disinfectant automatically by a corresponding switching of the valves and can also be flushed with a liquid.

What is claimed is:

1. An apparatus for filling a batch-type dialysis machine (D1) with a dialysis liquid, said apparatus comprising:
   at least one liquid container for reception of a liquid;
   at least one of a concentrate receptacle for reception of a concentrate and a concentrate connection for connection of a container holding the concentrate; and
   at least one preparation unit arranged and configured such that the liquid from the liquid container is mixed with the concentrate from at least one of the concentrate receptacle and the container holding the concentrate,
   said apparatus being separate from the batch-type dialysis machine, and mobile independently of the batch-type dialysis machine.

2. The apparatus in accordance with claim 1, wherein the preparation unit and the concentrate receptacle are configured as a same component.

3. The apparatus in accordance with claim 1, wherein the preparation unit is arranged and configured such that it is flushed by the liquid from the liquid container in operation of the apparatus.

4. The apparatus in accordance with claim 1, further comprising a first connector for dispensing of the dialysis liquid to the batch-type dialysis machine, said first connector being in communication with or connectable to the preparation unit.

5. The apparatus in accordance with claim 4, further comprising a second connector for reception of consumed dialysis liquid from a batch-type dialysis machine (D2) for emptying of the batch-type dialysis machine (D2).

6. The apparatus in accordance with claim 5, further comprising a third connector for supply of a gas or of a cleaning liquid to the batch-type dialysis machine (D2).

7. The apparatus in accordance with claim 6, wherein the second connector and the third connector are received in a common adapter.

8. The apparatus in accordance with claim 6, further comprising a conveying device arranged and configured to convey a gas or a liquid to the third connector.

9. The apparatus in accordance with claim 6, further comprising a container for receiving of a disinfectant arranged in a line between the conveying device and the third connector, with the container being arranged to dispense the disinfectant to the gas or the cleaning liquid flowing through the line.

10. The apparatus in accordance with claim 6, further comprising a fourth connector via which the liquid is supplied to the liquid container.

11. The apparatus according to claim 10, wherein the liquid is RO water.

12. The apparatus in accordance with claim 1, further comprising a conveying device arranged and configured to convey at least one of the liquid from the liquid container into the preparation unit, and a mixture of the liquid and the concentrate from the preparation unit to the batch-type dialysis machine (D1).

13. The apparatus in accordance with claim 12, further comprising a connector for supply of a gas or of a cleaning liquid to a batch-type dialysis machine (D2), and
   wherein the conveying device is arranged and configured such that the gas or the cleaning liquid is conveyed to the connector therewith.

14. The apparatus in accordance with claim 12, wherein the conveying device is a pump or a compressor.

15. The apparatus in accordance with claim 1, further comprising a unit for producing RO water.

16. The apparatus in accordance with claim 1, further comprising a heating device to heat at least one of the liquid located in the liquid container, the liquid supplied to the liquid container, and the liquid flowing out of the liquid container.

17. The apparatus in accordance with claim 1, further comprising a heating device to heat at least one of the preparation unit and the mixture flowing out of the preparation unit.

18. The apparatus according to claim 1, wherein the apparatus drains the dialysis liquid from the batch-type dialysis machine.

19. The apparatus according to claim 1, wherein the liquid is RO water.

20. A method of filling a batch-type dialysis machine (D1) with a dialysis liquid, comprising:
   providing an apparatus that includes at least one liquid container for reception of a liquid, at least one of a concentrate receptacle for reception of a concentrate and a concentrate connection for connection of a container holding the concentrate, and at least one preparation unit arranged and configured such that the liquid from the liquid container is mixed with the concentrate from at least one of the concentrate receptacle and the container holding the concentrate, the apparatus being separate from, and mobile independently of, the batch-type dialysis machine (D1);
producing the dialysis liquid in the apparatus; and
dispensing the dialysis liquid to the batch-type dialysis machine (D1) with the apparatus.

21. The method in accordance with claim 20, wherein the dialysis liquid is produced in the apparatus from the at least one liquid and the at least one concentrate, with both the liquid and the concentrate being stored in the apparatus.

22. The method in accordance with claim 21, wherein the concentrate is presented in the preparation unit,
wherein the preparation unit is flushed with the liquid for producing the dialysis liquid, and
wherein the produced dialysis liquid is then supplied to the batch-type dialysis machine (D1).

23. The method according to claim 21, wherein the at least one liquid is RO water.

24. The method in accordance with claim 20, wherein compressed air is generated by a compressor, and
wherein the compressed air conveys thr liquid out of the liquid container into the preparation unit in which the liquid is mixed with the concentrate.

25. The method in accordance with claim 20, wherein compressed air is generated by a compressor, and
wherein the compressed air is supplied to a batch-type dialysis machine (D2) in which the dialysis liquid is displaced from the batch-type dialysis machine (D2).

26. The method in accordance with claim 25, wherein a disinfectant is supplied to the compressed air before the compressed air is supplied to the batch-type dialysis machine (D2).

27. The method in accordance with claim 20, wherein compressed air is conveyed from a compressor into the liquid container in a first operating mode in which the batch-type dialysis machine (D1) is filled with the dialysis liquid, and
wherein the compressed air is conveyed from the compressor to a batch-type dialysis machine (D2) in a second operating mode in which the batch-type dialysis machine (D2) is emptied of the dialysis liquid.

28. The method in accordance with claim 27, wherein the compressed air is first supplied to the batch-type dialysis machine (D2) in the second operating mode for the emptying of the batch-type dialysis machine (D2), and is displaced from the batch-type dialysis machine (D2) by the dialysis liquid, and
wherein subsequently the compressed air is supplied to the liquid container for flushing of the batch-type dialysis machine (D2), such that via the compressed air the liquid is supplied from the liquid container to the batch-type dialysis machine (D2).

29. The method in accordance with claim 20, wherein compressed air is generated by a compressor, and
wherein the compressed air conveys the liquid out of the liquid container into a batch-type dialysis machine (D2) for flushing the batch-type dialysis machine (D2).

* * * * *

UNITED STATES PATENT AND TRADEMARK OFFICE
CERTIFICATE OF CORRECTION

PATENT NO.       : 8,671,996 B2                                           Page 1 of 1
APPLICATION NO. : 12/449775
DATED            : March 18, 2014
INVENTOR(S)      : Weilhoefer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1171 days.

Signed and Sealed this

Twenty-ninth Day of September, 2015

Michelle K. Lee
*Director of the United States Patent and Trademark Office*